United States Patent [19]

Hernestam et al.

[11] 4,021,563

[45] May 3, 1977

[54] METHOD OF TREATING CARDIAC ARRHYTHMIA WITH γ-PIPERIDINO-BUTYROPHENONES

[76] Inventors: Sven Eric Harry Hernestam, AB Ferrosan, P.O. Box S-201 10, Malmo 1, Sweden, S-201 10; Erling Niels Petersen, 52 Falkehusene, Albertslund, Denmark, DK-2620

[22] Filed: Feb. 2, 1976

[21] Appl. No.: 654,728

[30] Foreign Application Priority Data

Feb. 6, 1975 United Kingdom ............... 5030/75

[52] U.S. Cl. .................................... 424/267
[51] Int. Cl.² ................................... A61K 31/445
[58] Field of Search .......................... 424/267

[56] References Cited

UNITED STATES PATENTS 3,816,433  6/1974  Hernestam et al. ............... 424/267

OTHER PUBLICATIONS

Conn, Current Therapy (1970) pp. 155–159.

*Primary Examiner*—Stanley J. Friedman
*Attorney, Agent, or Firm*—Gordon W. Hueschen

[57] ABSTRACT

Therapeutic treatment of cardiac arrhythmia in mammals by oral or parenteral administration of certain substituted γ-piperidino-butyrophenones or the acid-addition salts thereof.

5 Claims, No Drawings

4,021,563

METHOD OF TREATING CARDIAC ARRHYTHMIA WITH γ-PIPERIDINO-BUTYROPHENONES

BACKGROUND OF THE INVENTION

This invention relates to a method for treating cardiac arrhythmia in mammals by administering a 4-fluoro-γ-(4-alkylpiperidino)-butyrophenone or a 4-fluro-γ-(4,4-dialkylpeperidino)-butyrophenone or an acid-addition salt thereof. Heretofore a great number of different compounds have been investigated in an effort to develop effective drugs for therapeutic treatment or cardiac arrhythmia (hereinafter referred to as arrhythmia). In animal tests many of these compounds have shown antiarrhythmic effect, but have not been acceptable for clinical use, because of low activity and/or side effects. Pharmacologically the carbamoyloxy decahydroquinoline derivative L 7810 (4-carbamoyloxyl-1-(4-fluorophenyl)-4-oxobutyl)decahydroquinoline) has been reported (Bagwell et al., Br. J. Pharmacol. 1973:48:183 – 93) to exert antiarrhythmic properties. By way of example, the prior art has employed for therapeutic treatment lidocaine, procainamide, quindine, propranolol, etc., compounds having activity as antiarrhythmic agents, but at the same time producing various toxic effects.

SUMMARY OF THE INVENTION

Our invention is based on the discovery that certain substituted γ-piperidino-butyrophenones are active antiarrhythmic agents, which exhibit both prophylactic and curative effect without producing toxic effects. The substituted γ-piperidino-butyrophenones of the present invention may be represented by the following general formula:

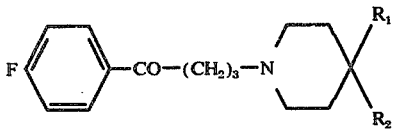

where $R_1$ and $R_2$ are, independently, hydrogen or lower alkyl, having 1 to 4 carbon atoms, e.g. methyl, ethyl, propyl, isopropyl, butyl, or isobutyl.

Compounds of the formula, in which R1 is hydrogen, has previously been reported to be active as local anaesthetics, anticonvulsants, psycho-sedatives, analgetics, and antidepressants (U.S. Pat. No. 3,816,433 and Brit. Pat. No. 1,142,143). The butyrophenonederivatives employed in the method of this invention can be administered orally or parenterally in combination with non-toxic pharmaceutical liquid or solid carriers.

DETAILED DESCRIPTION OF THE INVENTION

The substituted γ-piperidino-butyrophenones of the present invention form non-toxic acid-addition salts with a variety of pharmaceutically acceptable organic or inorganic salt-forming reagents.

Thus, acid-addition salts formed by admixture of a γ-piperidino-butyrophenone base with an equivalent of an acid, suitably in a neutral solvent, are formed with such acids as sulfuric, phosphoric, hydrocloric, hydrobromic, citric, lactic, tartaric, acetic, and related acids. For purposes of this invention, the substituted γ-piperidino-butyrophenones are equivalent to their non-toxic acid-addition salts. The antiarrhythmic activity of the compounds of the present invention compared with that of some clinically used antiarrhythmic drugs was determined as follows. The compounds were tested for their ability to prevent and reverse ouabain-induced arrhythmias in conscious rabbits, and the method used was essentially according to Basil et al. (Brit. J. Pharmacol. 1974, 50, 323 - 33).

Intravenous infusion of ouabain to conscious rabbits produces ventricular arrhythmias of short duration. An increase in the minimal dose of ouabai required to produce an arrhythmia may be taken as a measure of the antiarrhythmic action of the drug.

METHOD

PROPHYLACTIC EFFECT

12 Control experiments with physiol. Saline have shown that the arrhythmogenic dose of ouabain was rather constant in the same rabbit, when tested on tow consecutive days. In all experiments with drug treatment the control dose of ouabain required to produce arrhythmias in an animal was obtained the day before.

The test compound was administered intravenously to rabbits 1 minute before the ouabain challenge and the arrhythmogenic dose of ouabain after treatment was evaluated in per cent of the control arrhythmogenic dose. If this dose amounts to more the 110 % of the control arrhythmogenic dose recorded the day before, the test compound is regarded as having antiarrhymic activity.

Curative effect

A substance was considered curative, if it was able to reverse the ouabain-induced arrhythmia for at least 1 min. within 10 minutes after the injection.

A comparison of antiarrhythmic activity was performed between two compounds of the present invention a) metylperone and FG 5226, viz., (4-fluoro-γ-(4-ethyl-4-n-propyl-piperidino)-butyrophenone) and b) four clinically used antiarrhythmic drugs, lidocaine, procainamide, guinidine, and propranolol. Control animals got physiological saline, The results are given in Table 1.

Metylperone 0.1 mg/kg and FG 5226 0.1 mg/kg were more effective than lidocaine 1–5 mg/kg, procainamide 1-10 mg/kg, quinidine 1 mg/kg, and propranolol 0.5 mg/kg, and equiactive with quinidine 10 mg/kg, and propranolol 2 mg/kg. In contrast to metylperone and FG 5226 the active doses of the known antiarrhytmic drugs produced various toxic effects. The main effect of these low doses of compounds according to the present invention is presumably a central anatisympathetic effect.

Intravenous injection of methylperone 10 – 50 mg has been shown to inhibit ventricular arrhythmia in patients with myocardial infarction without producing side effects. Equi-antiarrhythmic doses of previously used drugs produce various cardiovascular side effects as well as agitation and confusion.

In contrast to the clinically used antiarrhythmic agents metylperone has a tranquilizing effect, which is of therapeutic benefit in patients with cardiac disease. Several patients with cardiac rhythm distrubances have hyperfunction of the sympathetic nervous system and anxiety, which presumably is caused by cardiac pain. The sympathetic hyperfunction induces increased levels of circulating catecholamines (Mc Donald et al. Lancet 1969, 4, 10 21–23; Jewitt et al. Lancet 1969, 3, 635–41; Siggers et al. Brit. Heart J. 1971, 33, 878–83), which is known to be arrhythmogenic and to have a direct effect on the heart. Metylperone is a neuroleptic, Some other nueroleptics (e.g. chlorpormazine) are also central sympatholytics, but they are contraindicated in patients with cardiac rhythm disturbances due to their potentiation of catecholamines (Tuck, Europ, Clin. Pharmacol 1973, 6, 81–87). This effect increases the arrhythmogenecity of the catecholamines and the cardiac function would be aggravated seriously. Metylperone does not potentiate the cardiac effects of catecholamines (E. Petersen, Acta Pharmacol. et Toxicol. 1974, 35 suppl. I, 49) L 7810 antagonizes ouabain-induced ventricular tachycardia and fibrillation in anaesthetized guinea pigs in dosage 0.3 – 3 mg/kg, but has also been found to inhibit arrhythmia induced by aconitine, which in contrast to ouabain has mainly peripheral effects. Metylperone 0.1 – 10.0 mg/kg has no aconitine inhibitory effect. Therefore L 7810 and metylperone presumably have a different mechanism of action.

more times a day. For oral use the dose is usually 20 – 50 mg three times. a day.

Clinical Tests

All patients with ventricular extrasystoles (VES) admitted to a coronary care unit suspected of having acute myocardial infraction are included in the investigation. This was carried out in a double-blind manner with metylperone against placebo (metylperone injectable without metylperone). When a patient arrives at the unit, he is monitored on an oscilloscope for registration of the electrocardiogram (ECG). In a 1 hour long period of observation the patient is characterized in respect to the type and the frequency of the arrhythmia. Depending on this and on the estimated age of the infraction, the patient is distributed to one of four groups. A bottle (metylperone or placebo) is chosen from a box, containing identical bottles, and in the following 10 minutes a total of 50 mg metylperone (or placebo) is injected intravenously as 5 injections with 2 min. intervals. The EGG registration is continued for 2

TABLE 1

| | | | prophylactic effect | | | curative effect |
|---|---|---|---|---|---|---|
| substance | dose mg/kg i.v. | number of rabbits | arrhythmogenic dose of ouabain increased to more than 110 %. number of rabbits | arrhythmogenic dose of ouabain in % of control arrhythmogenic dose $m \pm SD$ | p value x) in comparison to physiol. saline | number of rabbits reversed-/tested |
| Metylperone | 0.1 | 4 | 3 | $129 \pm 20$ | < .005 | 5/5 |
|  | 1.0 | 4 | 3 | $126 \pm 30$ | < .05 | 5/5 |
| FG 5226 | 0.1 | 4 | 3 | $109 \pm 21$ | > .05 | 3/4 |
|  | 1.0 | 4 | 1 | $93 \pm 18$ | > .05 | 2/4 |
| Lidocaine | 1.0 | 4 | 0 | $73 \pm 25$ | < .05 | 1/3 |
|  | 5.0 | 5 | 0 | $91 \pm 21$ | > .05 | 2/4 |
| Procainamide | 1.0 | 4 | 2 | $111 \pm 18$ | > .05 | 0/4 |
|  | 10.0 | 4 | 1 | $104 \pm 20$ | > .05 | 2/4 |
| Quinidine | 1.0 | 4 | 2 | $104 \pm 10$ | > .05 | 2/4 |
|  | 10.0 | 4 | 3 | $131 \pm 42$ | < .05 | 4/4 |
| Propranolol | 0.5 | 4 | 2 | $98 \pm 28$ | > .05 | 1/5 |
|  | 2.0 | 4 | 3 | $121 \pm 26$ | < 0.05 | 4/4 |
| Physiol. saline | — | 12 | 2 | $96 \pm 14$ | — | — | x) student's test

Metylperone is extremely active (0.1 mg/kg) against ouabain-induced ventricular tachycardia in conscious rabbits. Ouabain is known to produce arrhythmia by a central mechanism (Gillis et al. J. Pharmacol. Exp. Ther. 1972:183:154–68). The most probable explanation for these findings is, that methylperone in low doses depresses heart rhythm regulating centers in the hypothalamus without having any direct effect on the heart, i.e., a membrane stabilizing effect on the heart.

The lack of side effects during treatment of cardiac arrhythmia with metylperone may be due to the high antiarrhytmic potency, the tranquilizing anxiety-relieving effect, and the absence of catecholamine potentiating effect.

The compounds of the present invention can be administered orally or parenterally to mammals to prevent or to cure cardiac arrhythmia. The dosage administered will depend on the mammal involved, its age, weight, severity of arrhythmia, and intention of the treatment, if it is a curative or a prophylactic one. Illustratively, a dosage of the active compound will generally range from less than about 0.05 to about 2 mg (milligram) per kg (kilogram) of body weight.

For human use the intravenous dose can be 50 mg given during a 10 min. period, and if needed repeated hours. All ECGes in the three hours period are analyzed manually and the arrhythmias are recorded according to frequency and type. The psychic status and the cardiovascular status are checked several times during the three hours.

The results are given in Table 2 and show that metylperone has an antiarrhythmic effect in patients with acute myocardial infarction.

The following (Preparations and Examples) are given by way of illustration only:

Preparation

Compounds of formula I in which $R_1$ is hydrogen, and $R_2$ is an alkyl group are obtainable by procedures as described in the literature, e.g. U.S. Pat. No. 3,816,433, British. Pat. No. 1,142,474, and British Pat. No. 1,142,143, both published Feb. 5, 1969. A process for the preparation of these compounds comprises reacting a piperidine, which is alkylated in the paraposition with γ-halogeno-p-fluoro-butyrophenone, at an elevated temperature, and in the presence of an acid binding agent. Using another process the compounds are prepared by a Grignard synthesis by reacting the appropiate 4-alkylpiperidino-butyronitirle with p-fluoro-bromobenzene.

TABLE 2

| substance | | control hour mean total VES ± SD | 0 – 60 min. after inj. mean total VES ± SD | 61 – 120 min. after inj. mean total VES ± SD |
|---|---|---|---|---|
| AMI | metylperone N = 6 | 372 ± 148 | 212 ± 138 | 93 ± 89[a] |
|  | placebo N = 3 | 370 ± 169 | 418 ± 394 | 644 ± 815 |
| not AMI | metylperone N = 2 | 321 ± 18 | 251 ± 85 | 348 ± 28 |
|  | placebo N = 3 | 685 ± 250 | 643 ± 290 | 695 ± 240 |

[a] p = 0.003 (student's t-test)
VES : ventricular extrasystoles
AMI : acute myocardial infarction Compounds of formula I, when $R_1$ and $R_2$ are alkyl, alkyl groups can be prepared using the same process. In this way the compounds can be prepared by reacting the appropiate 4,4-di-alkyl substituted piperidines with γ-halogeno-p-fluro-butyrophenone, or by reacting the appropriate 4, 4-dialkyl-piperidino-butyronitrile with p-fluorobromobenzene.

The compounds of the invention, together with conventional pharmaceutical carriers, can be employed in unit dossages forms such as solids, for example, tablets or capsules or liquid solutions, suspensions or elixirs for oral administration, and injections, or liquid solutions, emulsions, and the like for parenteral use.

EXAMPLE 1

4-fluoro-γ-(4-ethyl-4-n-propyl-piperidino)-butyrophenone

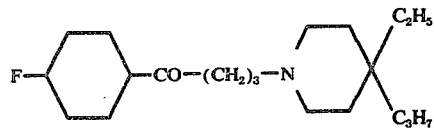

20.1 gms. (0.1 mole) of γ-chloro-p-fluorobutyrophenone, 15.5 gms. (0.1 mole) of 4-ethyl-4-n-propylpiperidine, 11.1 grms. (0.1 + 10%) triethylamine and 90 mls. of xylene, and a minor amount of potassium iodine were introduced into a 250 ml. round bottomed reaction flask provided with a reflux condenser and a heating mantle. The mixture was refluxed for 5 hours and cooled to room temperature. The triethylamine hydrochloride obtained was sucked off and washed on the filter with three 50 ml. portions of benzene. The mother liquors were combined and 250 ml. of ether were added. The solution was washed with three 10 ml. portions of water and then filtered over active carbon and dried over sodium sulphate. The solution was filtered and evaporated to dryness. The evaporation residue was distilled for obtaining 19.2 gms. (60% of theory) of te product, γ-(4-ethyl-4-n-propyl-piperidine-p-fluorobutyrophenone. Boiling point 140°– 143° C/0.1 mms. of Hg.

The base was dissolved in ether and the γ-(4-ethyl-4-n-propyl-piperidine)-p-fluorobutyrophenone precipitated as the hydrochloride by adding alcoholic hydrochloric acid and ether. M.P. 185° C.

EXAMPLE 2

The following 4-fluoro-γ-(4, 4-dialkyl-piperidino)-butyrophenones are prepared from the corresponding 4,4-dialkyl-piperidines by reaction with γ-chloro-p-fluorobutyrophenone according to the procedure of Example 1.

4-fluoro-γ-(4-methyl-4-n-hexyl-piperidinol)-butyrophenone, M.P. 220° C.
4-fluoro-γ-(4-methyl-4-ethyl-piperidino)-butyrophenone, M.P. 243° – 246° C.
4-fluoro-γ-(4-ethyl-4-n-butyl-piperidino)-butyrophenone, M.P. 176° – 179° C.
4-fluoro-γ-(4-methyl-4-n-propyl-piperidino)-butyrophenone, M.P. 230° – 231° C.

All M.P.s refer to hydrochlorides.

EXAMPLE 3

γ-(4,4-diethylpiperidino)-p-fluorobutyrophenone hydrochloride.

To a Grignard solution, prepared from 70.0 gms. (0.4 mole) of p-fluorobromobenzene, and 98 gms. (0.4 mole) of magnesium in 500 mls. of tetrahydrofuran, 20.8 gms. (0.1 mole) of γ-(4,4-diethylpiperidino)-butyronitrile dissolved in 200 mls. of ether, was added dropwise. After the addition the reaction mixture was refluxed for 3 hours, whereupon the reaction product wad decomposed with saturated ammonium chloride solution. The separated etherphase was evaporated, and the residue (crude ketionine) boiled for 20 hours with 500 mls. of 5 N hydrochloric acid. After cooling an excess of conc. ammonia was added, and the reaction mixture was extracted with ether. The dried ether was evaporated and the residue distilled in vacuum. 23 gms. of the compound was obtained at 140° – 145° C/0.01 mms. of Hg. (75% of theory).

The hydrochloride was prepared according to the procedure of Example 1. M.P. 214° – 217° C.

Example 4

The following γ-(4,4-dialkylpiperidino)-butyrophenones are prepared from the corresponding γ-(4,4-dialkylpiperidino)butyronitriles by reaction with a Grignard solution prepared from magnesium and p-fluorobromobenzene according to the procedure of Example 3.

4-fluoro-γ-(4-ethyl-4-iso-butyl-piperidino)-butyrophenone, M.P. 180° C.
4-fluoro-γ-(4,4-di-n-propyl-piperidino)-butyrophenone, M.P. 163° – 165° C.
4-fluoro-γ-(4-methyl-4-amyl-piperidino)-butyrophenone, M.P. 216° – 218° C.
4-fluoro-γ-(4,4-dimethyl-piperidino)-butyrophenone, M.P. 238° – 242° C.

All M.P.s refer to hydrochlorides.

EXAMPLE 5

Sterile Solution of Injection

The following pharmaceutical compositions are formulated with the indicated amount of active agent using conventional technique.

| Ingredients | Weight (mg) |
| --- | --- |
| Metylperone (4-fluoro-γ-(4-methyl-piperidino)-butyrophenone hydrochloride) | 20 |
| Sodium chloride | 9.3 |
| Sodium dihydrogen phosphate | 5.08 |
| Disodium edetate (ethylenediaminetetra-acetic acid disodium salt) | 0.2 |
| Benzyl alcohol | 40 |
| Sodium hydroxide | q.s. to adjust pH at 5.9 – 6.1 |
| Water double-distilled | q.s. to 2 ml |

Filtration through Membrane Filter, aseptic filling into ampoule, and treatment in autoclave with streaming vapour for twenty minutes.

EXAMPLE 6

Tablets

Tablets suitable for oral administration which contain the following ingredients may be prepared by conventional techniques.

| Ingredients | Weight (mg) |
| --- | --- |
| 4-fluoro-γ-(4-ethyl-4-n-propyl-piperidino)-butyrophenone hydrochloride | 5 |
| Magnesium stearate | 3 |
| Cellulose powder | 6 |
| Talcum | 3 |
| Lactose | 143 |
| Aerosil | 1 |

The gamma-piperidinobutyrophenone compounds of the foregoing examples 1, 2, 3, and 4 are active antiarrhythmia compounds in the tests reported under "Method" and may be embodied in pharmaceutical compositions as illustratively shown in examples 5 and 6.

It is to be understood that the invention is not to be limited to the exact details of operation or exact compounds, compositions, methods, or procedures shown and described, as obvious modifications and equivalents will be apparent to one skilled in the art.

We claim:

1. A method of treating arrhythmia in a living animal body in need of such treatment, comprising the step of orally or parenterally administering to said living animal body an effective anti-arrhythmic amount of a compound selected from the group consisting of γ-piperidino-butyrophenone of the formula:

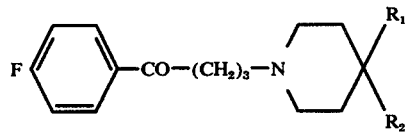

where $R_1$ and $R_2$ are independently hydrogen or lower alkyl, having 1 to 4 carbon atoms, and pharmaceutically acceptable acid addition salts thereof.

2. The method of claim 1, wherein the compound is 4-fluoro-γ-(4-methyl-piperidino)-butyrophenone hydrochloride.

3. The method of claim 1, wherein the compound is 4-fluoro-γ-(4-ethyl-4-n-propyl-piperidino)-butyrophenone hydrochloride.

4. The method of claim 1, wherein said effective dosage comprises from about 0.05 milligrams to about 2 miligrams per kilogram of body weight.

5. The method of claim 1, wherein the compound is employed in admixture or conjunction with pharmaceutically acceptable carriers.

* * * * *

UNITED STATES PATENT OFFICE
CERTIFICATE OF CORRECTION

Patent No. 4,021,563     Dated May 3, 1977

Inventor(s) Sven Eric Henry Hernestam and Erling Niels Petersen

It is certified that error appears in the above-identified patent and that said Letters Patent are hereby corrected as shown below:

Column 1, lines 9-10; change "4-fluro-γ-(4,4-dialkylpeperidino)-" to read ---4-fluoro-γ-(4,4-dialkylpiperidino)- ---.

Column 1, line 20; change "carbamoyloxyl-1-" to read ---carbamoyloxy-1- ---.

Column 1, line 25; change "quindine," to read ---quinidine,---.

Column 1, line 47; change "Compounds of the formula," to read ---Compounds of this formula,---.

Column 1, line 62; change "hydrocloric," to read ---hydrochloric,---.

Column 2, line 16; change "with physiol. Saline" to read ---with physiol. saline---.

Column 2, line 18; change "when tested on tow" to read ---when tested on two---.

Column 2, line 23; change "ouabain challenge and" to read ---ouabain challenge, and---.

Column 2, line 63; change "distrubances" to read ---disturbances---.

Column 3, line 4; change "(e.g. chlorpormazine) to read ---(e.g. chlorpromazine)---.

Column 3, line 62; change "and intention" to read ---and the intention---.

Column 4, line 7; change "infraction" to read ---infarction---.

Column 4, line 16; change "infraction," to read ---infarction,---.

Column 4, line 21; change "The EGG" to read ---The ECG---.

UNITED STATES PATENT OFFICE
CERTIFICATE OF CORRECTION

Patent No. 4,021,563          Dated May 3, 1977

Inventor(s) Sven Eric Henry Hernestam and Erling Niels Petersen

It is certified that error appears in the above-identified patent and that said Letters Patent are hereby corrected as shown below:

Column 4, line 67; change "4-alkylpiperidino-butyronitirle" to read ---4-alkylpiperidino-butyronitrile---.

Column 5, lines 20-21; change "are alkyl,alkyl groups" to read ---are both alkyl groups,---.

Column 5, line 29; change "dossages" to read ---dosage---.

Column 5, lines 45-46; change "fluorobutyrophene-one, 15.5 gms." to read ---fluorobutyrophenone, 15.5 gms.---.

Column 5, line 61; change "of te product," to read ---of the product,---.

Column 5, line 61; change "-piperidine-p-" to read --- -piperidine)-p- ---.

Column 6, line 31; change "wad" to read ---was---.

Column 8, line 33; change "2 miligrams" to read ---2 milligrams---.

Signed and Sealed this

Thirteenth Day of September 197

[SEAL]

Attest:

RUTH C. MASON
*Attesting Officer*

LUTRELLE F. PARKER
*Acting Commissioner of Patents and Trademark*